United States Patent
Wu et al.

(10) Patent No.: US 11,900,048 B2
(45) Date of Patent: Feb. 13, 2024

(54) ACQUISITION METHOD AND SYSTEM FOR CLINICAL EXPERIMENTAL DATA, ELECTRONIC DEVICE, AND STORAGE MEDIUM

(71) Applicants: Shenzhen People's Hospital, Shenzhen (CN); Beijing Tsinghua Changgung Hospital, Beijing (CN)

(72) Inventors: Meilong Wu, Shenzhen (CN); Xiaobin Feng, Beijing (CN); Shizhong Yang, Beijing (CN); Liping Liu, Shenzhen (CN); Chengquan Li, Beijing (CN); Xiaojuan Wang, Beijing (CN); Yusen Zhang, Shenzhen (CN); Linsen Liu, Shenzhen (CN); Tianchong Wu, Shenzhen (CN); Jiahong Dong, Shenzhen (CN)

(73) Assignees: SHENZHEN PEOPLE'S HOSPITAL, Shenzhen (CN); BEIJING TSINGHUA CHANGGUNG HOSPITAL, Beijing (CN)

( * ) Notice: Subject to any disclaimer, the term of this patent is extended or adjusted under 35 U.S.C. 154(b) by 0 days.

(21) Appl. No.: 18/351,549

(22) Filed: Jul. 13, 2023

(65) Prior Publication Data
US 2024/0020461 A1    Jan. 18, 2024

(30) Foreign Application Priority Data
Jul. 14, 2022   (CN) .......................... 202210827456.X

(51) Int. Cl.
*G06F 40/166*   (2020.01)
*G16H 10/20*   (2018.01)
(Continued)

(52) U.S. Cl.
CPC ............. *G06F 40/166* (2020.01); *G06V 30/10* (2022.01); *G10L 15/08* (2013.01); *G16H 10/20* (2018.01); *G16H 40/20* (2018.01)

(58) Field of Classification Search
CPC ........ G16H 40/20; G16H 10/20; G06V 30/10; G10L 15/08
See application file for complete search history.

(56) References Cited

U.S. PATENT DOCUMENTS

| | | | |
|---|---|---|---|
| 2014/0288964 A1* | 9/2014 | Zillner | G16H 50/20 705/3 |
| 2021/0193297 A1* | 6/2021 | Buckland | G16H 40/20 |

(Continued)

FOREIGN PATENT DOCUMENTS

| | | |
|---|---|---|
| CN | 109461477 A | 3/2019 |
| CN | 111699533 A | 9/2020 |

OTHER PUBLICATIONS

CNIPA, Notification of a First Office Action for CN202210827456.X, dated Sep. 9, 2022.

(Continued)

*Primary Examiner* — Tadesse Hailu
(74) *Attorney, Agent, or Firm* — Zhigang Ma

(57) ABSTRACT

An acquisition method and system for clinical experimental data, an electronic device, and a storage medium are provided, which relate to the field of data processing technologies, the method includes: extracting first clinical experimental data from a target information system based on a preset clinical experimental data extraction model; acquiring and labeling speech input data and manual input data of a target user to obtain second clinical experiment data; recognizing to —be-extracted clinical experimental data based on a preset character recognition model to obtain third clinical experimental data; organizing and arranging the three clinical experimental data in chronological order and (Continued)

weight to generate ultimate clinical experimental data. Thus, problems of difficulty in connectivity and high error rate caused by inability to integrate various acquisition methods for clinical experimental data are solved, multimodal data extraction and automatic information quality proofreading are implemented based on integrating various acquisition methods for clinical experimental data.

9 Claims, 7 Drawing Sheets

(51) Int. Cl.
  *G06V 30/10* (2022.01)
  *G10L 15/08* (2006.01)
  *G16H 40/20* (2018.01)

(56) References Cited

U.S. PATENT DOCUMENTS

2022/0084633 A1* 3/2022 Das .................. G16H 50/20
2022/0084662 A1* 3/2022 Das .................. A61B 5/02055

OTHER PUBLICATIONS

Beijing Qingyi Intelligent Technology Co., Ltd. and Hangzhou Tigermed Consulting Co., Ltd. (Applicants), Reply to Notification of a First Office Action for CN202210827456.X, w/ replacement claims, Sep. 16, 2022.
Beijing Qingyi Intelligent Technology Co., Ltd. and Hangzhou Tigermed Consulting Co., Ltd. (Applicants), Supplemental Reply to Notification of a First Office Action for CN202210827456.X, w/ (allowed) replacement claims, Sep. 22, 2022.
CNIPA, Notification to grant patent right for invention in CN202210827456.X, dated Sep. 28, 2022.

* cited by examiner

Due to a development of medical science and technology, theoretical knowledge and clinical practice in this field are constantly changing. With new research and experience continue to expand our knowledge structure, it is necessary or appropriate to make appropriate adjustments in practice, medical treatment, and medication. Readers are advised to check the latest information of relevant operations or the latest product information provided by each drug manufacturer, and determine the recommended dose, administration method, administration time and related contraindication of drugs under the guidance of clinical practitioners. It is the responsibility of the attending physician to establish a diagnosis based on their understanding and relevant experience of the patient, determine the dosage and optimal treatment method for each patient, and take appropriate safety precautions. Neither the publisher nor the author shall be liable for any personal injury and/or property damage that may occur during the use of this publication.

FIG. 5

Take an L-shaped incision in the upper abdomen, enter the abdomen layer by layer, and protect the incision.

Upon exploration, there was no obvious ascites in the abdominal cavity, there is no obvious adhesion in abdominal cavity, no bleeding point is found, and a field of vision is clean, and mild liver cirrhosis was observed.

The tumor is located at the junction of liver S5 and S6, with clear boundaries and a size of approximately 3.1 cm × 3.3 cm, not protruding from the liver surface. There is no tumor of or nodule in the left liver, and the right posterior lobe resection is planned.

Right liver and perihepatic ligament. Behind the right liver and adrenal gland, towards the head, towards the makuuchi ligament.

FIG. 6

Looking up at the starry sky, down-to-earth

Upon careful exploration, no obvious ascites was found

ACQUISITION METHOD AND SYSTEM FOR CLINICAL EXPERIMENTAL DATA, ELECTRONIC DEVICE, AND STORAGE MEDIUM

TECHNICAL FIELD

The disclosure relates to the field of data processing technologies, and more particularly to an acquisition method and system for clinical experimental data, an electronic device, and a storage medium.

BACKGROUND

With development of information technology, clinical experimental data can be acquired by three manners including accessing of a database, inputting of a mobile terminal, and scanning document to extract characters at present. Meanwhile, researches for the clinical experimental data in project practice also have many explorations, clinical research regulations and regulatory aspects also constantly introduce guidelines for improvement. Life science industry in a post pandemic era is rapidly shifting towards a decentralized clinical experimental method, so as to achieve a purpose of highly valuing data quality and compliance.

However, a management system for clinical experiment in the related art did not effectively integrate the three manners, and has problems of difficulty in connectivity and high error rate in recognizing different forms of documents. How to effectively combine different data acquisition methods, achieve multimodal data extraction and automatic quality proofreading to obtain more complete and high-quality research data is an urgent need for researchers.

SUMMARY

The disclosure provides an acquisition method and system for clinical experimental data, an electronic device, and a storage medium, which is to solve problems of difficulty in connectivity and high error rate caused by inability to effectively integrate various acquisition methods for clinical experimental data in related art, multimodal data extraction and automatic information quality proofreading in clinical experiments are implemented based on artificial intelligence.

A first aspect embodiment of the disclosure provides an acquisition method for clinical experimental data, and the method includes: extracting first clinical experimental data from a target information system based on a preset extraction model for clinical experimental data; acquiring at least one of speech input data or manual input data of a target user, and labeling the at least one of speech input data or manual input data to obtain second clinical experimental data; recognizing to-be-extracted clinical experimental data based on a preset character recognition model to obtain third clinical experimental data; and organizing and arranging the first clinical experimental data, the second clinical experimental data and the third clinical experimental data according to at least one of a chronological order or a weight of at least one of the first clinical experimental data, the second clinical experimental data and the third clinical experimental data to generate ultimate clinical experimental data.

In an embodiment, before the organizing and arranging the first clinical experimental data, the second clinical experimental data and the third clinical experimental data according to at least one of a chronological order or a weight of at least one of the first clinical experimental data, the second clinical experimental data and the third clinical experimental data to generate ultimate clinical experimental data, the acquisition method for clinical experimental data further includes: simulating the first clinical experimental data, the second clinical experimental data, and the third clinical experimental data, to obtain a first labor cost of the first clinical experimental data, a second labor cost of the second clinical experimental data, and a third labor cost of the third clinical experimental data, respectively; determining whether each of the first labor cost, the second labor cost and the third labor cost is less than or equal to a preset labor cost threshold; in a situation that each of the first labor cost, the second labor cost and the third labor cost is less than or equal to the preset labor cost threshold, organizing and arranging the first clinical experimental data, the second clinical experimental data and the third clinical experimental data according to the chronological orders of the first clinical experimental data, the second clinical experimental data, and the third clinical experimental data to generate the ultimate clinical experimental data; in a situation that each of one or two of the first labor cost, the second labor cost and the third labor cost is less than or equal to the preset labor cost threshold, organizing and arranging the first clinical experimental data, the second clinical experimental data and the third clinical experimental data based on at least one of a chronological order or a weight of clinical experimental data corresponding to each of the one or two of the first labor cost, the second labor cost and the third labor cost which are less than or equal to the preset labor cost threshold to generate the ultimate clinical experimental data.

In an embodiment, the organizing and arranging the first clinical experimental data, the second clinical experimental data and the third clinical experimental data according to at least one of a chronological order or a weight of at least one of the first clinical experimental data, the second clinical experimental data and the third clinical experimental data to generate ultimate clinical experimental data, includes: acquiring a first weight corresponding to the first clinical experimental data, a second weight corresponding to the second clinical experimental data, and a third weight corresponding to the third clinical experimental data; organizing and arranging, based on the first weight, the second weight, and the third weight, the first clinical experimental data, the second clinical experimental data and the third clinical experimental data in a preset order, to generate the ultimate clinical experimental data.

In an embodiment, before the extracting first clinical experimental data from a target information system based on a preset extraction model for clinical experimental data, the acquisition method for clinical experimental data further includes: recognizing enrollment staffs from the target information system based on at least one of a preset keyword category or a keyword number, in a situation that during a recognition process, at least one of the keyword category meeting a first threshold or the keyword number meeting a second threshold is satisfied, determining the enrollment staffs meet an enrollment requirement, and enrolling the enrollment staffs in a clinical experiment group after performing information privacy processing of the enrollment staffs; comparing clinical experimental data of the enrollment staffs enrolled in the clinical experiment group and a classification standard, to acquire comparison passed clinical experimental data; constructing the preset extraction model for clinical experimental data by using the comparison passed clinical experimental data.

In an embodiment, before the recognizing to-be-extracted clinical experimental data based on a preset character recognition model to obtain third clinical experimental data, the acquisition method for clinical experimental data further includes: acquiring at least one of a to-be-recognized text or a to-be-recognized image; recognizing characters and a modifying sign based on a preset floating distance threshold to recognize the at least one of the to-be-recognized text or the to-be-recognized image to thus obtain recognized characters, concatenating the recognized characters based on a preset principle to obtain a recognized text; correcting the recognized text based on a preset comparative document to obtain a corrected recognized text, and training a model based on the corrected recognized text to obtain the preset character recognition model.

In an embodiment, after the training a model based on the corrected recognized text to obtain the preset character recognition model, the acquisition method for clinical experimental data further includes: updating the preset comparative document based on the corrected recognized text.

In an embodiment, the preset comparative document includes at least one of a preset character pattern, a dictionary, a book, or a medical transcription.

According to the acquisition method for clinical experimental data of embodiments in the disclosure, the first clinical experimental data is extracted from the target information system based on the preset extraction model for clinical experimental data, the at least one of speech input data or manual input data of the target user are acquired, and the at least one of speech input data or manual input data are labeled to obtain the second clinical experimental data, meanwhile, the to-be-extracted clinical experimental data is recognized based on the preset character recognition model to obtain the third clinical experimental data, and the three clinical experimental data (i.e., first clinical experimental data, second clinical experimental data and third clinical experimental data) are organized and arranged according to the at least one of the chronological order or the weight of at least one of the three clinical experimental data to generate the ultimate clinical experimental data. Thus, the problems of difficulty in connectivity and high error rate caused by inability to effectively integrate various acquisition methods for clinical experimental data are solved, multimodal data extraction and automatic information quality proofreading in clinical experiments are implemented based on integrating various acquisition methods for clinical experimental data and artificial intelligence.

A second aspect embodiment of the disclosure provides an acquisition system for clinical experimental data, and the system includes an extraction module, an acquisition module, a recognition module and a generation module.

The extraction module is configured to extract first clinical experimental data from a target information system based on a preset extraction model of clinical experimental data.

The acquisition module is configured to acquire at least one of speech input data or manual input data of a target user, and label the at least one of speech input data or manual input data to obtain second clinical experimental data.

The recognition module is configured to recognize to-be-extracted clinical experimental data based on a preset character recognition model to obtain third clinical experimental data.

The generation module is configured to organize and arrange the first clinical experimental data, the second clinical experimental data and the third clinical experimental data according to at least one of a chronological order or a weight of at least one of the first clinical experimental data, the second clinical experimental data and the third clinical experimental data to generate ultimate clinical experimental data.

In an embodiment, before the extracting first clinical experimental data from a target information system based on a preset extraction model for clinical experimental data, the generation module is further configured to simulate the first clinical experimental data, the second clinical experimental data and the third clinical experimental data, to obtain a first labor cost of the first clinical experimental data, a second labor cost of the second clinical experimental data, and a third labor cost of the third clinical experimental data, respectively; determine whether each of the first labor cost, the second labor cost and the third labor cost is less than or equal to a preset labor cost threshold; in a situation that each of the first labor cost, the second labor cost and the third labor cost is less than or equal to the preset labor cost threshold, organize and arrange the first clinical experimental data, the second clinical experimental data and the third clinical experimental data according to the chronological orders of the first clinical experimental data, the second clinical experimental data and the third clinical experimental data to generate the ultimate clinical experimental data; in a situation that each of one or two of the first labor cost, the second labor cost and the third labor cost is less than or equal to the preset labor cost threshold, organize and arrange the first clinical experimental data, the second clinical experimental data and the third clinical experimental data based on at least one of a chronological order or a weight of clinical experimental data corresponding to each of the one or two of the first labor cost, the second labor cost and the third labor cost to generate the ultimate clinical experimental data.

In an embodiment, the generation module is configured to acquire a first weight corresponding to the first clinical experimental data, a second weight corresponding to the second clinical experimental data, and a third weight corresponding to the third clinical experimental data, and organize and arrange, based on the first weight, the second weight, and the third weight, the first clinical experimental data, the second clinical experimental data and the third clinical experimental data in a preset order, to generate the ultimate clinical experimental data.

In an embodiment, before the extracting first clinical experimental data from a target information system based on a preset extraction model for clinical experimental data, the extraction module is further configured to recognize enrollment staffs from the target information system based on at least one of a preset keyword category or a keyword number, in a situation that during a recognition process, at least one of the keyword category meeting a first threshold or the keyword number meeting a second threshold is satisfied, determine that the enrollment staffs meet an enrollment requirement, and enroll the enrollment staffs in a clinical experiment group after performing information privacy processing of the enrollment staffs, compare the clinical experimental data of the enrollment staffs enrolled in the clinical experiment group and a classification standard, to acquire comparison passed clinical experimental data, and construct the preset extraction model for clinical experimental data by using the comparison passed clinical experimental data.

In an embodiment, before the recognizing to-be-extracted clinical experimental data based on a preset character recognition model to obtain third clinical experimental data, the recognition module is further configured to acquire at least one of a to-be-recognized text or a to-be-recognized image, recognize characters and a modifying sign based on a preset floating distance threshold to recognize at least one of the to-be-recognized text or the to-be-recognized image to thus obtain recognized characters, concatenate the recognized characters based on a preset principle to obtain a recognized text; \ correct the recognized text based on a preset comparative document to obtain a corrected recognized text, and train a model based on the corrected recognized text to obtain the preset character recognition model.

In an embodiment, after the training a model based on the corrected recognized text to obtain the preset character recognition model, the recognition module is further configured to update the preset comparative document based on the corrected recognized text.

In an embodiment, the preset comparative document includes at least one of a preset character pattern, a dictionary, a book, or a medical transcription.

According to the acquisition system for clinical experimental data of embodiments in the disclosure, the first clinical experimental data is extracted from the target information system based on the preset extraction model for clinical experimental data, the at least one of speech input data or manual input data of the target user are acquired, and the at least one of speech input data or manual input data are labeled to obtain the second clinical experimental data, meanwhile, the to-be-extracted clinical experimental data is recognized based on the preset character recognition model to obtain the third clinical experimental data, and the three clinical experimental data are organized and arranged according to at least one of the chronological order or the weight of the three clinical experimental data to generate the ultimate clinical experimental data. Thus, the problems of difficulty in connectivity and high error rate caused by inability to effectively integrate various acquisition methods for clinical experimental data are solved, multimodal data extraction and automatic information quality proofreading in clinical experiments are implemented based on integrating various acquisition methods for clinical experimental data and artificial intelligence.

A third aspect embodiment of the disclosure provides an electronic device, and the electronic device includes: a memory, a processor and a computer program stored in the memory, and the computer program is configured to be executed by the processor to implement the acquisition method for clinical experimental data as described in the above embodiments.

A fourth aspect embodiment of the disclosure provides a non-transitory computer-readable storage medium having a computer program stored therein, the computer program is configured to be executed by a processor to implement the acquisition method for clinical experimental data as described in the above embodiments.

Additional aspects and advantages of the disclosure will be partially provided in following description, which will become apparent from the following description, or learned through the practice of the disclosure.

BRIEF DESCRIPTION OF DRAWINGS

The above and/or additional aspects and advantages of the disclosure will become apparent and easy to understand from the description of embodiments in conjunction with drawings below.

FIG. 5 illustrates a schematic diagram of a regular text or image according to an embodiment of the disclosure.

FIG. 6 illustrates a schematic diagram of an irregular writing situation 1 according to an embodiment of the disclosure.

FIG. 7 illustrates a schematic diagram of an irregular writing situation 2 according to an embodiment of the disclosure.

DETAILED DESCRIPTION OF EMBODIMENTS

Embodiments of the disclosure are described in detail below, examples of the embodiments are shown in drawings, same or similar labels throughout represent same or similar components or components with same or similar functions. The above embodiments described by referring the drawings are exemplary, which intends to explain the disclosure and cannot be understand as a limitation on the disclosure.

An acquisition method and system for clinical experimental data, an electronic device, and a storage medium provided in the embodiments of the disclosure are described below by referring the drawings. Aiming at the above problems of difficulty in connectivity and high error rate caused by inability to effectively integrate various acquisition methods for clinical experimental data mentioned in background, the disclosure provides an acquisition method for clinical experimental data, in the method, first clinical experimental data is extracted form a target information system based on a preset extraction model for clinical experimental data, at least one of speech input data or manual input data of a target user is acquired, and the at least one of speech input data or manual input data is labeled to obtain second clinical experimental data, meanwhile, to-be-extracted clinical experimental data is recognized based on a preset character recognition model to obtain third clinical experimental data, and the three clinical experimental data (i.e., first clinical experimental data, second clinical experimental data and third clinical experimental data) are organized and arranged according to at least one of a chronological order or a weight of the three clinical experimental data to generate ultimate clinical experimental data. Thus, the problems of difficulty in connectivity and high error rate caused by inability to effectively integrate various acquisition methods for clinical experimental data are solved, multimodal data extraction and automatic information quality proofreading in clinical experiments are implemented based on integrating various acquisition methods for clinical experimental data and artificial intelligence.

Figure 1:
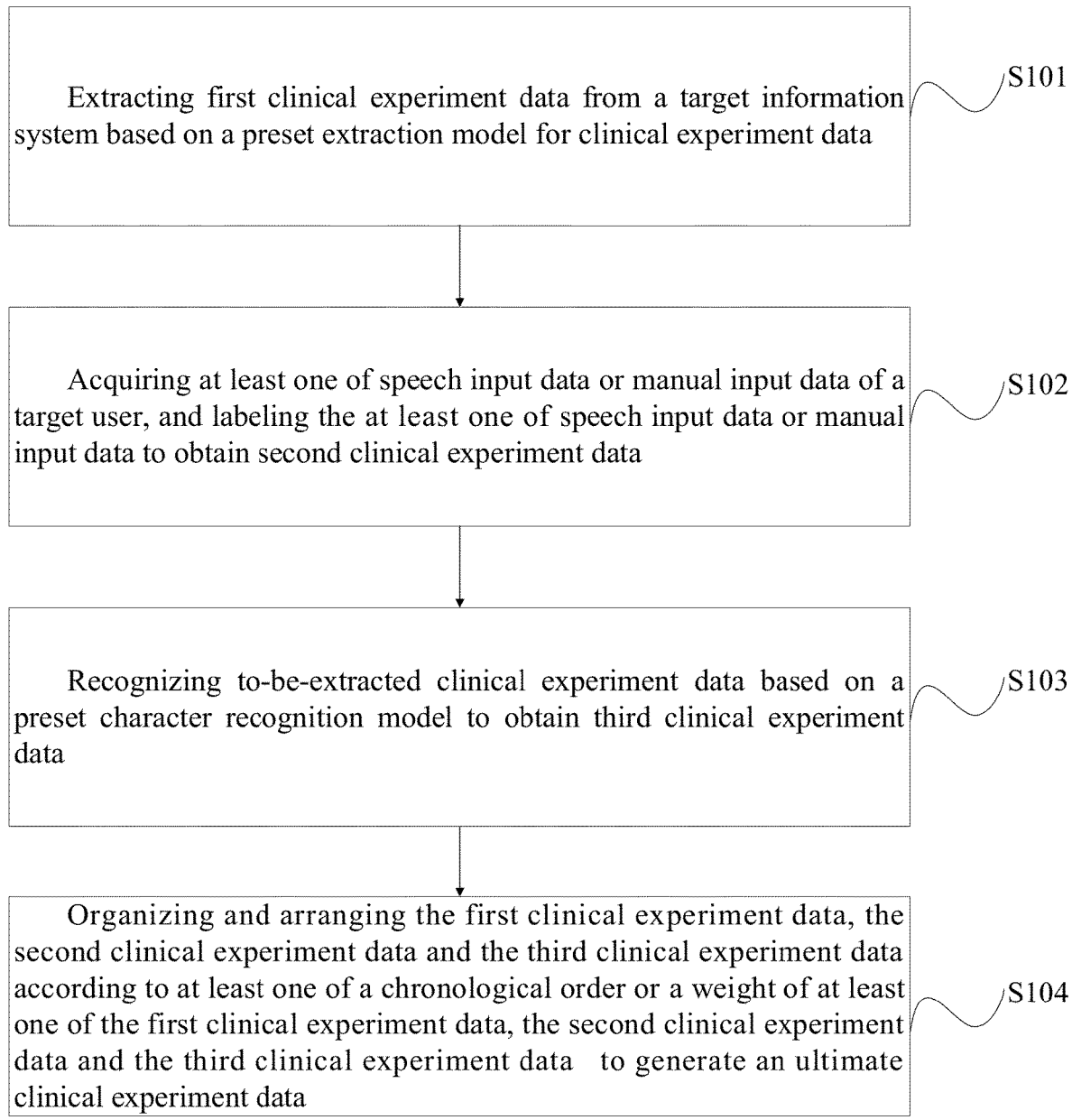
FIG. 1 illustrates a flowchart of an acquisition method for clinical experimental data according to an embodiment of the disclosure.

Specifically, FIG. 1 illustrates a flowchart of an acquisition method for clinical experimental data provided in the embodiments of the disclosure.

Figure 2:
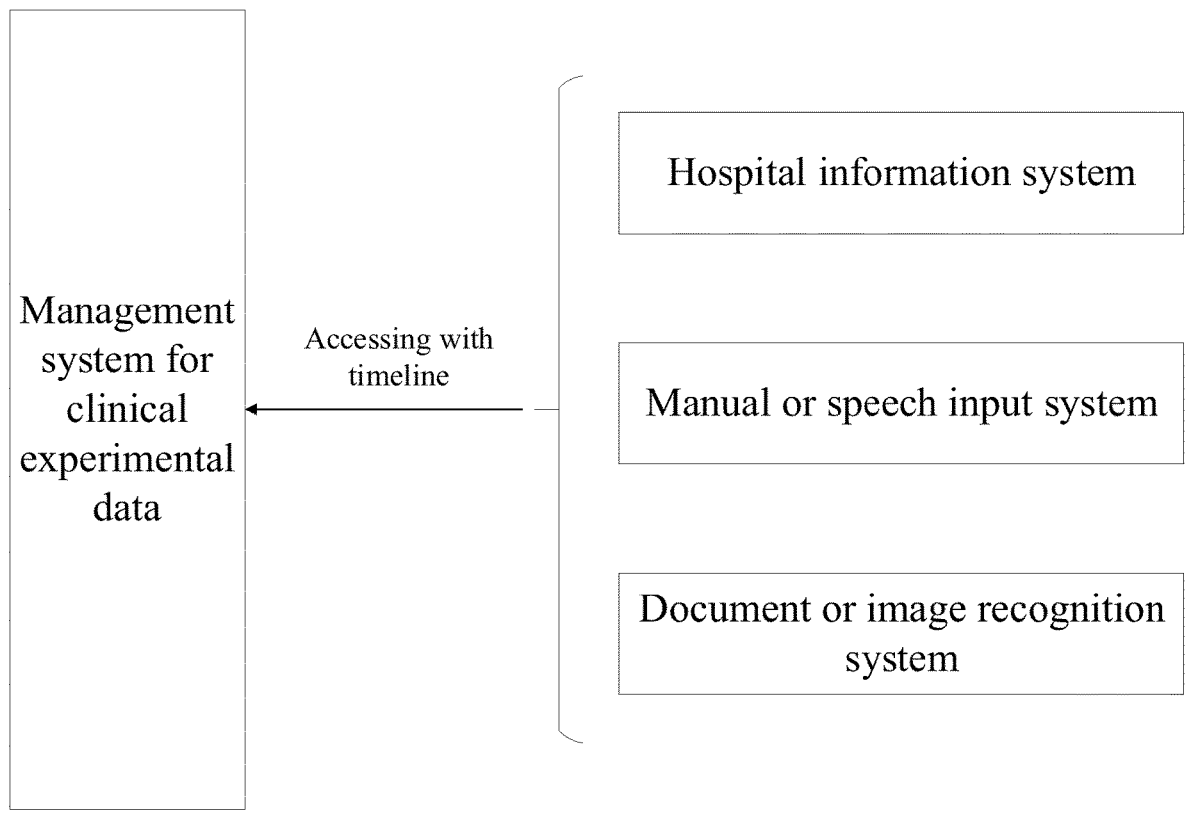
FIG. 2 illustrates a schematic diagram of a management system for clinical experimental data according to an embodiment of the disclosure.

Components of a management system for clinical experimental data used in the embodiments of the disclosure are introduced before introducing the acquisition method for clinical experimental data in the embodiments of the disclosure. As shown in FIG. 2, the management system for clinical experimental data includes: a hospital information system, a manual or speech input system and a document or image recognition system. Data acquisition processes of different systems are described in detail through the following specific embodiments.

As shown in FIG. 1, the acquisition method for clinical experimental data includes the following steps S101-S104.

In step S101, first clinical experimental data is extracted from a target information system based on a preset extraction model for clinical experimental data.

In an embodiment, before the extracting first clinical experimental data from a target information system based on a preset extraction model for clinical experimental data, the acquisition method for clinical experimental data further includes the following steps, enrollment staffs are recognized from the target information system based on at least one of a preset keyword category or a keyword number, in a situation that during a recognition process, at least one of the keyword category meeting a first threshold or the keyword number meeting a second threshold is satisfied, it is determined that the enrollment staffs meet an enrollment requirement, and the enrollment staffs are enrolled in a clinical experiment group after performing information privacy processing of the enrollment staffs; clinical experimental data of the enrollment staffs enrolled in the clinical experiment group is compared with a classification standard to acquire comparison passed clinical experimental data (i.e., the clinical experimental data conforms to the classification standard); and the preset extraction model for clinical experimental data is constructed by using the comparison passed clinical experimental data.

Specifically, the first threshold and the second threshold can be set according to previous experimental experience, or preset thresholds of the keyword category and the keyword number are respectively obtained by calculating previous case data using calculation methods such as logistic regression, deep learning and machine learning, and the target information system can be the hospital information system.

Specifically, clinicians face some problems during consultation process with patients, due to busy work of the clinicians, and a large number of patients diagnosed and treated every day. On the one hand, if the clinicians individually recognize patients who meet clinical requirements, work progress of the clinicians will be affected; on the other hand, if the clinicians intermittently recognize patients who meet the clinical requirements, it may cause omissions of a large number of potential patients who meet the clinical requirements, so as to affect a treatment effect of the patients.

Figure 3:
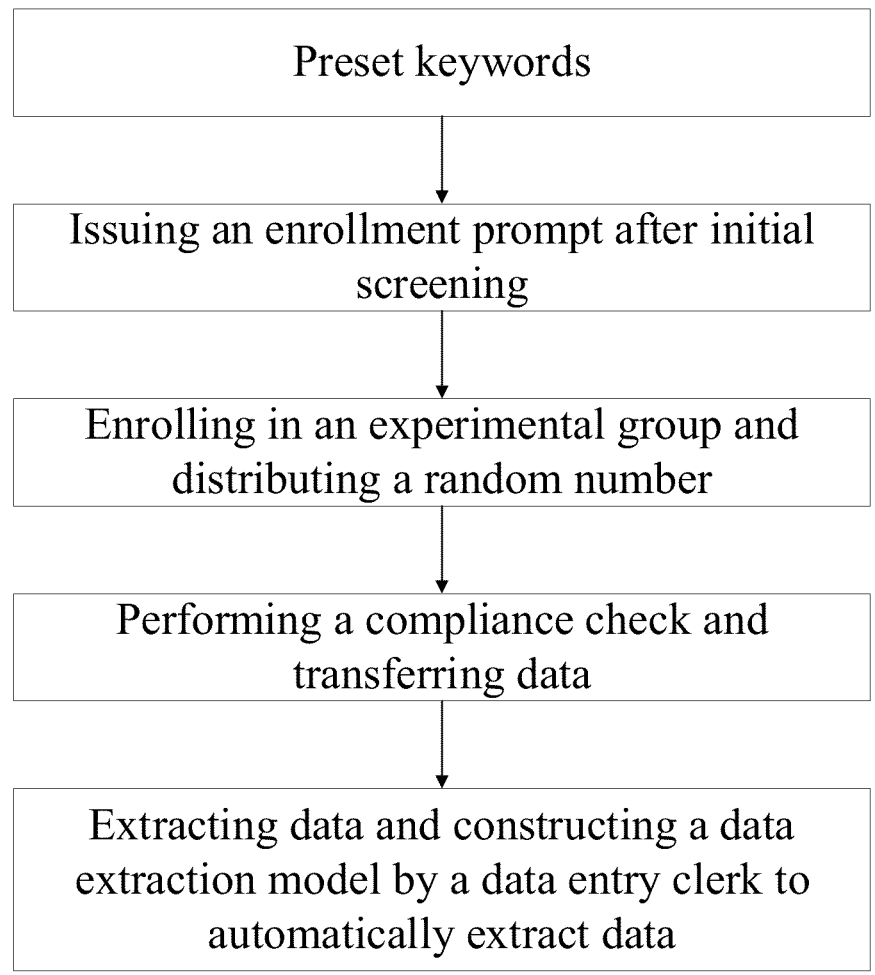
FIG. 3 illustrates a flowchart of a management system for clinical experimental data accessing to a hospital information system according to an embodiment of the disclosure.

Thus, as shown in FIG. 3, the management system for clinical experimental data is connected to the hospital information system and a keyword corresponding to clinical experiment is preset in the embodiments of the disclosure, a clinical experiment enrollment prompt is triggered when the keyword category and the keyword number reach the threshold preset by hospital, so as to recognize the enrollment staffs from the target information system, and the enrollment staffs are enrolled in the clinical experiment group after performing information privacy processing of the enrollment staffs.

For example, first, in a situation that at least one of the keyword category preset by the management system for clinical experimental data meeting the first threshold or the keyword number preset by the management system for clinical experimental data meeting the second threshold is satisfied, the clinical experiment enrollment prompt is triggered, the clinician can simply explain to a patient, and a professional is responsible for communication. In a situation that the recognized keyword category or the keyword number meets an enrollment condition, privacy processing is performed on information of the enrollment staffs, that is, in a situation that the patient meets the enrollment requirement, a random number is distributed to the patient, and the random number is used as an identity during experiment, which can avoid leakage of privacy information such as names, and avoid an interference caused by the identity to the clinical experiment.

Then, in a situation that the patient meets the enrollment requirement and the random number is distributed to the patient, information of the clinical experiment patient is extracted to a data compliance check module of an information system for clinical experiment to check the extracted patient whether implements necessary procedures for protecting patients in the clinical experiment such as ethical review and informed consent, and check the extracted clinical experimental data such as privately processed data whether reaches regulatory requirements for regulation, and the clinical experimental data is compared with the regulatory requirements and classification of data by regulations according to national regulatory requirements, purpose and content of research to acquire the comparison passed clinical experimental data, and the comparison passed clinical experimental data is inputted into a data extraction system.

Finally, the comparison passed clinical experimental data is extracted and marked by a data entry clerk, and the data extraction model is constructed, so as to automatically extract the clinical experimental data from the target information system through the data extraction model, and the clinical experimental data is the first clinical experimental data.

In step S102, at least one of speech input data or manual input data of a target user is acquired, and the at least one of speech input data or manual input data is labeled to obtain second clinical experimental data.

Specifically, the management system for clinical experimental data used in the embodiments of the disclosure further includes the manual or speech input system. That is, in addition to an entry interface for the data entry clerk, an interface for manually inputting data or speech inputting data for medical staffs and patients is set in a situation that the data entry clerk cannot enter data in time and the management system for clinical experimental data cannot be connected to the hospital information system caused by uncontrollable factors such as epidemic situation. It should be noted that a labelling processing is performed after inputting data by different experimenters, medical staffs and patients to ensure safety and reliability of data, that is, the data input by different experimenters, medical staffs and patients is labeled differently to recognize, so as to obtain the second clinical experimental data.

In an embodiment, after data inputting is implemented, the obtained data is corrected by the data entry clerk to obtain the second clinical experimental data, and positive incentive can be optionally given to the data entry clerk.

Specifically, before acquiring the at least one of speech input data or manual input data of the target user, typical keywords or sentences with inaccurate pronunciation of different area are collected in the embodiments of the disclosure, area and different regional language (dialect or mandarin) are determined, moreover, a distributed regional language recognition model and a distributed character processing model can be constructed based on the collected different regional pronunciation by the embodiments of the disclosure, so as to more accurately extract corresponding sentences, and improve accuracy of character extraction.

In step S103, to-be-extracted clinical experimental data is recognized based on the preset character recognition model to obtain third clinical experimental data.

In an embodiment, before the recognizing to-be-extracted clinical experimental data based on a preset character recognition model to obtain third clinical experimental data, the acquisition method for clinical experimental data further includes the following steps. At least one of a to-be-recognized text or a to-be-recognized image is acquired; characters and a modifying sign are recognized based on a preset floating distance threshold to recognize at least one of the to-be-recognized text or the to-be-recognized image to thus obtain recognized characters, the recognized characters are concatenated based on a preset principle to obtain a recognized text; the recognized text are corrected based on a preset comparative document to obtain a corrected recognized text, and a model is trained based on the corrected recognized text to obtain the preset character recognition model.

In an embodiment, after the training a model based on the corrected recognized text to obtain the preset character recognition model, the acquisition method for clinical experimental data includes the following steps. The preset comparative document is updated based on the corrected recognized text.

In an embodiment, the preset comparative document includes at least one of a preset character pattern, a dictionary, a book, or a medical transcription.

Figure 4:
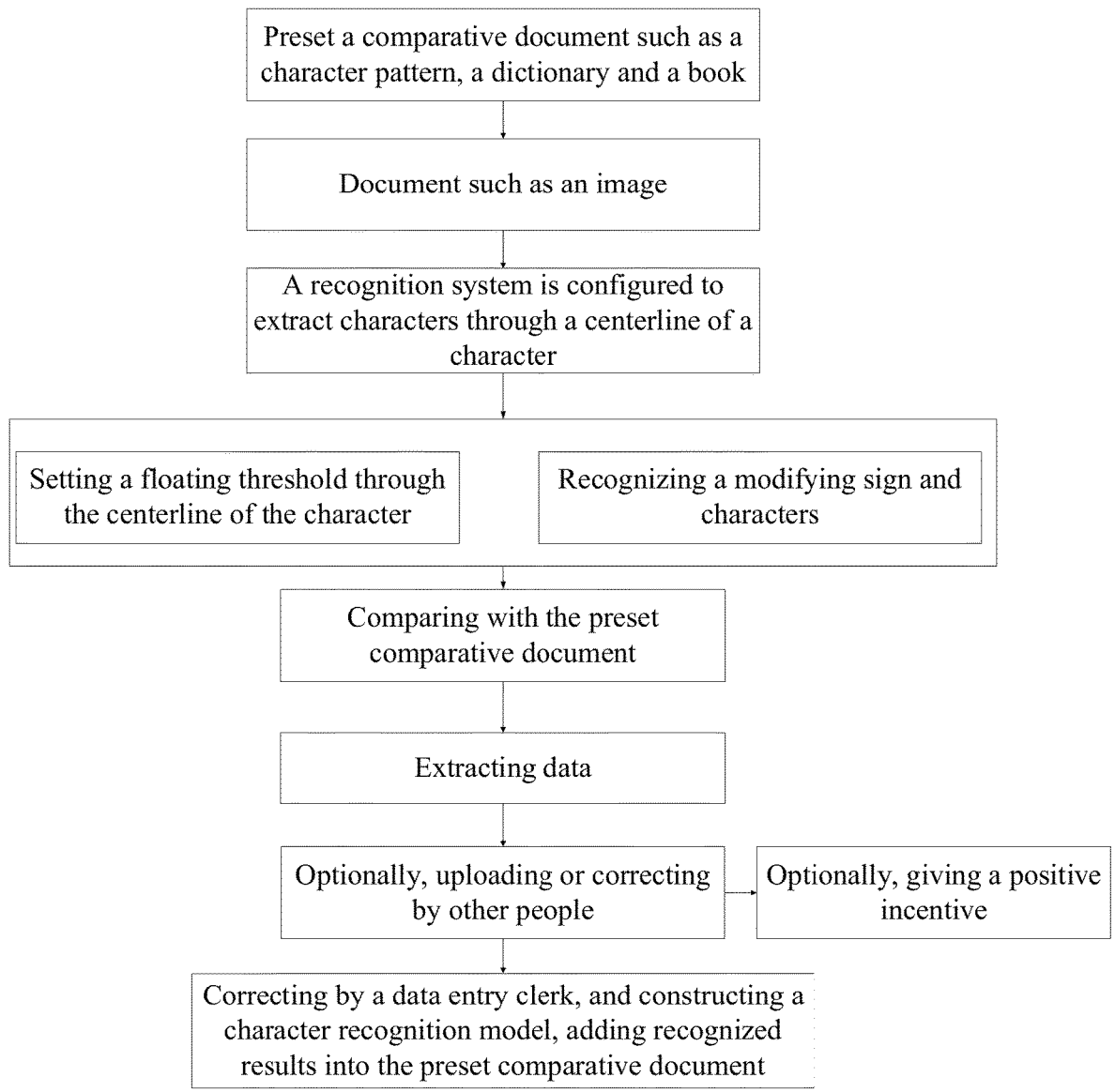
FIG. 4 illustrates a schematic diagram of a document or image recognition system of a management system for clinical experimental data according to an embodiment of the disclosure.

Specifically, as shown in FIG. 4, the management system for clinical experimental data provided in the embodiments of the disclosure further includes a document or image recognition system. A comparative document needs to be preset in the document or image recognition system, and the comparative document includes at least one of a character pattern such as regular script, running script, and cursive script, a dictionary, a book, or a medical transcription, which can compare subsequent recognized characters and determine a correctness of the subsequent recognized characters. At least one of a to-be-recognized text or a to-be-recognized image is acquired and at least one of the to-be-recognized text or the to-be-recognized image is transmitted to the document or image recognition system through a scanning process, a Bluetooth, a chat software, and a universal serial bus flash disk (U-disk). A floating distance threshold is automatically set based on size and centerline of a character to recognize characters and a modifying sign to recognize at least one of the to-be-recognized text or the to-be-recognized image to thus obtain recognized characters, the recognized characters are concatenated based on a nearby principle or a modifying-sign-based principle to obtain a recognized text, the recognized text is compared with the preset comparative document and a semantic and grammar check is performed, after recognizing and extracting characters to obtain recognized and extracted characters, the recognized and extracted characters are compared with original document by a upload staff, and recognized result is corrected by the upload staff, the positive incentive is given to the upload staff. A model is trained based on the corrected recognized text to obtain the preset character recognition model, and a new recognition result is added and enriched to the preset comparative document to obtain the third clinical experimental data.

It should be noted that due to an existence of various situations such as regular writing and irregular writing in a document image, setting of thresholds for different writing situations is different, the following two specific embodiments are used for describing in detail.

Specifically, FIG. 5 illustrates a regular document image, the threshold can be set for the document image through sizes and centerlines of the characters to better recognize and extract the characters, for example, a centerline is set at a position of a half of a vertical length of the sizes of the characters, and floating 50 percent (%) of a vertical distance is set as the threshold, in that situation, the characters can be better recognized and extracted, a horizontal threshold distance can be set for the characters with radicals and indexing components (i.e., Chinese character components) to recognize. For example, radicals and indexing components shown in words "science and technology" in Chinese (i.e., 科技) have a tiny negative distance, and radical and indexing component of a word "clinical" in Chinese (i.e., 临) has a tiny positive distance, so as to more clearly extract and recognize the corresponding characters through the horizontal threshold distance. After recognizing and extracting the characters, the recognized and extracted characters are compared with the preset comparative document and checked whether its semantics are smooth and complete.

In an embodiment, FIG. 6 illustrates a document image of an irregular writing situation 1, in the irregular writing situation (i.e., when identifying a handwritten document), deviation situations of the characters are different, and the deviation situations include a deviation situation of character during normal writing, and an abnormal writing situation such as a large distance separation occurred in the radical and indexing component during writing characters.

An example for the deviation situation of the characters occurred during normal writing is shown in FIG. 6. In a position a, a deviation in the characters exists at a line where the position a is located (not shown in FIG. 6), for normal writing, the characters on a same line may exhibit continuous and small fluctuations, that is the centerlines of the vertical direction and the vertical distances may exhibit continuous and small fluctuations, and the centerline and the threshold of the vertical direction are automatically detected and changed to achieve a continuous extraction for the characters.

At a position b in FIG. 6, the position b illustrates a situation of a sudden and drastic change in the centerline when there is a missing item in writing and correction is made, there is a modifying sign (not shown in FIG. 6) at the position b, the modifying sign indicates adding a word "enter" to the position b of the document, and the modifying sign is detected by the character recognition model at this time, the characters included or not included in the system are determined by comparing the characters with the preset comparative document and performing the semantic check. If a situation of unclear sentence and incomprehensible semantic caused by an absence of the word "enter" in Chinese (i.e. 进) in the position b can be determined by the system, then the characters at the position b are included in the system.

For correction of many characters, as shown in a position c of FIG. 6, there is a modifying sign (not shown in FIG. 6)

at the position c, the modifying sign indicates adding a sentence "there is no obvious adhesion in abdominal cavity, no bleeding point is found, and a field of vision is clean" to the position c of the document, the modifying sign is detected and recognized by the system, the characters indicated by the modifying sign are included in the modifying sign, and then compared with the preset comparative document, and the semantic check is performed. Obviously, the sentence "there is no obvious adhesion in abdominal cavity, no bleeding point is found, and a field of vision is clean" is consistent with expression and a semantic of the sentence is integral, if a second half of the sentence "no bleeding point is found, and a field of vision is clean" in the position c is not included in the modifying sign, a situation of semantic confusion will be caused, therefore, the former method is chosen to extract and organize the characters. Moreover, the character recognition system is configured to recognize a regular area of the characters appearing in a certain area to determine whether the characters in that area are corrected characters. As shown in Refer to FIG. 6, the sentence "there is no obvious adhesion in abdominal cavity, no bleeding point is found, and a field of vision is clean" appears in an obvious deviation area (not shown in FIG. 6), and the sentence cannot be well aligned with both the top and bottom lines, thus, the characters of the area are estimated as the corrected characters, and the characters of the area need to be organized according a nearby principle or a modifying-sign-based principle. Due to the modifying sign in the embodiment, the characters are corrected according to the modifying sign at first, and the characters are compared with the preset comparative document and the semantic check is performed.

When a situation shown in a position d of FIG. 6 appears during a writing process, there is an erasure symbol (not shown in FIG. 6) at the position d, and the erasure symbol indicates that a word "of" at the position d is deleted, corresponding characters cannot be matched by comparing with the preset comparative document, and a semantic of a sentence in the position d is fluent and integral without the characters, thus a correction in the position d will be filtered. If there is correction of the characters in a position e, a word "right" at the position e is above the line of the document text (not shown in FIG. 6), even though the correction cannot be recognized and there is no modifying sign, the word "right" can be recognized according to the centerline and the floating distance threshold, if the word "right" is not added, in a situation that a sentence "liver posterior lobectomy" is compared with the preset comparative document, an inaccurately semantic is discovered, liver merely has expressions such as "right posterior lobe of the liver and right liver posterior lobe", without the expression of a phrase or a noun "liver posterior lobe", thus the word "right" need be included in the sentence by comparing with the preset comparative document and performing the semantic check. If there is correction of the characters in a position f, there is an erasure symbol (not shown in FIG. 6) at the position f, the word "perihepatic" is close to both the top and bottom lines, and the word may be detected by both the centerline and the floating distance threshold, then a priority identification in a corrected position appears in both the top and bottom lines, and the word is compared with the preset comparative document and the semantic check is performed.

In an embodiment, in a situation that a large distance separation of the radical and indexing component appears in writing, in a position h and a position j of FIG. 6, there is a significant separation between the characters in the position j and the position h during writing (not shown in FIG. 6), in a situation that an adjacent horizontal distance threshold detection is performed, a word "cavity" in Chinese (i.e., 腔) may be recognized as a word "moon" in Chinese (i.e., 月) and a word "empty" in Chinese (i.e. 空), and a word "obvious" in Chinese (i.e., 明) is recognized as a word "sun" in Chinese (i.e., 日) and a word "moon" in Chinese (i.e., 月), at this time, the semantic is integral and fluent when a sentence "abdomen, moon, and empty" in Chinese (i.e., 腹月空) is matched as a sentence "abdominal cavity" in Chinese (i.e., 腹腔), and a sentence "no, sun, moon, display, and abdominal dropsy" in Chinese (i.e., 尤日月显腹水) is matched as a sentence "no obvious abdominal dropsy" in Chinese (i.e., 无明显腹水) by comparing with the preset comparative document. Therefore, the characters are included in the system by adopting the sentence "abdominal cavity" in Chinese and the sentence "no obvious abdominal dropsy" in Chinese rather than included according to the horizontal distance threshold. Although an integral character can be recognized in the first time by setting the horizontal distance threshold, in a situation that different writing habits make the characters separate further, a situation of integral character divided by a large horizontal distance of the radical and indexing component can be avoided by comparing with the preset comparative document and performing the semantic check, which can avoid a problem of incoherent semantic appeared. A distance threshold processing for font with upper and lower combination structure is similar with the horizontal distance threshold processing, and the distance threshold processing for font with upper and lower combination structure includes a longitudinal distance detection, a comparison of the preset comparative document, and a semantic check.

In an embodiment, according to the above processing method, in a document image of a situation of irregular writing 2 shown in FIG. 7, a position a is compared with the preset comparative document to discover that a word "say" in Chinese (i.e., 曰) and a word "born" in Chinese (i.e., 生) should be determined as a word "star" in Chinese (i.e., 星), a word "say" in Chinese (i.e., 曰) and a word "work" in Chinese (i.e., 业) in a position b should be determined as a word "obvious" in Chinese (i.e., 显). Moreover, after recognizing the document or image, the recognized result is artificially determined by the upload staff or other people, and the positive incentive is optionally given to them, the data enter clerk is configured to perform correction and construct the character recognition model, add and enrich accurate identification results to the preset comparative document.

In step S104, the first clinical experimental data, the second clinical experimental data and the third clinical experimental data are organized and arranged according to at least one of a chronological order or a weight of at least one of the first clinical experimental data, the second clinical experimental data and the third clinical experimental data to generate ultimate clinical experimental data.

In an embodiment, before the organizing and arranging the first clinical experimental data, the second clinical experimental data and the third clinical experimental data according to at least one of a chronological order or a weight of at least one of the first clinical experimental data, the second clinical experimental data and the third clinical experimental data to generate ultimate clinical experimental data, the acquisition method for clinical experimental data further includes the following steps. A first weight corresponding to the first clinical experimental data, a second weight corresponding to the second clinical experimental data, and a third weight corresponding to the third clinical experimental data are obtained; the first clinical experimental data, the second clinical experimental data and the third clinical experimental data are organized and arranged based on the first weight, the second weight, the third weight in a preset order to generate the ultimate clinical experimental data.

In an embodiment, the first clinical experimental data, the second clinical experimental data and the third clinical experimental data can be organized and arranged according to the chronological order of at least one of the first clinical experimental data, the second clinical experimental data and the third clinical experimental data to generate the ultimate clinical experimental data in the embodiments of the disclosure. For example, in the embodiments of the disclosure, a time corresponding to the first clinical experimental data is 8 o'clock, a time corresponding to the second clinical experimental data is 9 o'clock, and a time corresponding to the third clinical experimental data is 10 o'clock, the first clinical experimental data, the second clinical experimental data and the third clinical experimental data can be organized and arranged according to an order of the first clinical experimental data, the second clinical experimental data and the third clinical experimental data to generate the ultimate clinical experimental data in the embodiments of the disclosure; for another example, in the embodiments of the disclosure, the time corresponding to the second clinical experimental data is 8 o'clock, the time corresponding to the first clinical experimental data is 9 o'clock, and the time corresponding to the third clinical experimental data is 10 o'clock, the first clinical experimental data, the second clinical experimental data and the third clinical experimental data can be organized and arranged according to an order of the second clinical experimental data, the first clinical experimental data and the third clinical experimental data to generate the ultimate clinical experimental data in the embodiments of the disclosure.

In an embodiment, the first clinical experimental data, the second clinical experimental data and the third clinical experimental data can be organized and arranged based on the weight to generate the ultimate clinical experimental data in the embodiments of the disclosure. For example, in the embodiments of the disclosure, the first weight corresponding to the first clinical experimental data is 35%, the second weight corresponding to the second clinical experimental data is 45%, and the third weight corresponding to the third clinical experimental data is 20%, the first clinical experimental data, the second clinical experimental data and the third clinical experimental data can be organized and arranged according to an order of the second clinical experimental data, the first clinical experimental data and the third clinical experimental data to generate the ultimate clinical experimental data in the embodiment of the disclosure, that is, in the embodiments of the disclosure, a sort order for organizing and arranging is generated based on importance of the first clinical experimental data, the second clinical experimental data and the third clinical experimental data, so as to generate the ultimate clinical experimental data based on the latest sorting order.

In an embodiment, the first clinical experimental data, the second clinical experimental data and the third clinical experimental data can be organized and arranged according to the chronological order and the weight of at least one of the first clinical experimental data, the second clinical experimental data and the third clinical experimental data to generate the ultimate clinical experimental data in the embodiments of the disclosure. Where time priority is greater than weight priority. For example, in the embodiments of the disclosure, the time corresponding to the first clinical experimental data is 8 o'clock, and the corresponding first weight is 35%, the time corresponding to the second clinical experimental data is 7 o'clock, and the corresponding first weight is 45%, the time corresponding to the third clinical experimental data is 10 o'clock, and the corresponding first weight is 20%, the first clinical experimental data, the second clinical experimental data and the third clinical experimental data can be organized and arranged according to an order of the second clinical experimental data, the first clinical experimental data and the third clinical experimental data to generate the ultimate clinical experimental data in the embodiment of the disclosure. For another example, in the embodiments of the disclosure, the time corresponding to the first clinical experimental data is 8 o'clock, and the corresponding first weight is 30%, the time corresponding to the second clinical experimental data is 8 o'clock, and the corresponding first weight is 20%, the time corresponding to the third clinical experimental data is 9 o'clock, and the corresponding first weight is 50%, due to the same time corresponding to the first clinical experimental data and the second clinical experimental data, the first clinical experimental data and the second clinical experimental data can be arranged according to priority of the first clinical experimental data and the second clinical experimental data in the embodiments of the disclosure, that is the first clinical experimental data, the second clinical experimental data and the third clinical experimental data can be organized and arranged according to an order of the first clinical experimental data, the second clinical experimental data and the third clinical experimental data to generate the ultimate clinical experimental data in the embodiment of the disclosure.

In an embodiment, before the organizing and arranging the first clinical experimental data, the second clinical experimental data and the third clinical experimental data according to at least one of a chronological order or a weight of at least one of the first clinical experimental data, the second clinical experimental data and the third clinical experimental data to generate ultimate clinical experimental data, the acquisition method for clinical experimental data further includes the following steps. The first clinical experimental data, the second clinical experimental data and the third clinical experimental data are simulated to obtain a first labor cost of the first clinical experimental data, a second labor cost of the second clinical experimental data, and a third labor cost of the third clinical experimental data, respectively; whether each of the first labor cost, the second labor cost and the third labor cost is less than or equal to a preset labor cost threshold is determined; in a situation that each of the first labor cost, the second labor cost and the third labor cost is less than or equal to the preset labor cost threshold, the first clinical experimental data, the second clinical experimental data and the third clinical experimental data are organized and arranged according to the chronological order of at least one of the first clinical experimental data, the second clinical experimental data and the third clinical experimental data to generate the ultimate clinical experimental data; in a situation that each of the first labor cost, the second labor cost and the third labor cost is less than or equal to the preset labor cost threshold, the first clinical experimental data, the second clinical experimental data and the third clinical experimental data are organized and arranged based on at least one of a chronological order or a weight of clinical experimental data corresponding to each of the one or two of the first labor cost, the second labor cost and the third labor cost to generate the ultimate clinical experimental data.

The preset labor cost threshold can be a threshold set by the hospital according to labor cost required for the clinical experimental data, and the preset labor cost threshold can also be a threshold obtained by multiple calculations and simulations, and no specific restrictions will be made here. Specifically, three different clinical experimental data (i.e., the first clinical experimental data, the second clinical experimental data and the third clinical experimental data) can be pre-simulated by the embodiments of the disclosure to obtain the corresponding labor costs and weights separately, and sizes of the corresponding labor costs and the preset labor cost threshold are separately determined to further organize and arrange. The corresponding weights of the three clinical experimental data are determined by a size of each of the labor costs, the higher the cost, the greater the corresponding weight proportion, and the lower the cost, the smaller the corresponding weight proportion, it can be set according to actual situation, and no specific restrictions will be made here.

Specifically, the corresponding labor costs of the three clinical experimental data can be obtained based on costs, time other aspects of the clinical experimental data in the embodiments of the disclosure. A maximum value of the labor cost is assumed as 10, the preset labor cost threshold is 8, if the first labor cost of the first clinical experimental data, the second labor cost of the second clinical experimental data, and the third labor cost of the third clinical experimental data are 6, 7 and 8 respectively, that each of the labor costs of the three clinical experimental data is less than or equal to the preset labor cost threshold, at this time, the first clinical experimental data, the second clinical experimental data and the third clinical experimental data are organized and arranged according to the chronological order of at least one of the first clinical experimental data, the second clinical experimental data and the third clinical experimental data to generate the ultimate clinical experimental data; if the first labor cost of the first clinical experimental data is 6, the second labor cost of the second clinical experimental data is 7, and the third labor cost of the third clinical experimental data is 9, in a situation that each of one or two of the first labor cost, the second labor cost and the third labor cost is less than or equal to the preset labor cost threshold, the first clinical experimental data, the second clinical experimental data and the third clinical experimental data are organized and arranged according to at least one of the chronological order or the weight of clinical experimental data corresponding to each of the one or two of the first labor cost, the second labor cost and the third labor cost, that is organized and arranged according to at least one of the chronological order or the weight of the first clinical experimental data and the second clinical experimental data to generate the ultimate clinical experimental data.

Figure 8:
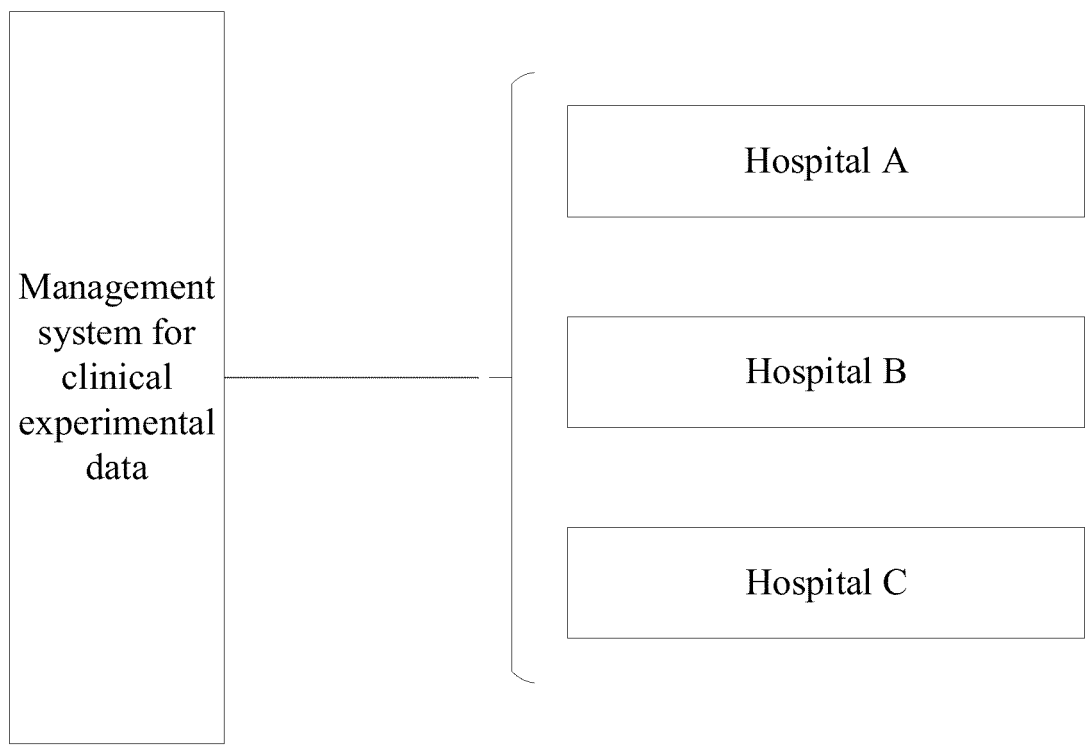
FIG. 8 illustrates a schematic diagram of a management system for clinical experimental data docked with various hospitals or experimental institutions according to an embodiment of the disclosure.

It should be noted that, as shown in FIG. 8, different hospitals and clinical experimental institutions are connected by the management system for clinical experimental data. For example, the clinical experimental data of the hospital A, the clinical experimental data of the hospital B and the clinical experimental data of the hospital C are separately connected with the management system for clinical experimental to synchronously obtain the clinical experimental data from different hospitals.

According to the acquisition method for clinical experimental data of embodiments in the disclosure, the first clinical experimental data is extracted from the target information system based on the preset extraction model for clinical experimental data, the at least one of speech input data or manual input data of the target user are acquired, and the at least one of speech input data or manual input data are labeled to obtain the second clinical experimental data, meanwhile, the to-be-extracted clinical experimental data is recognized based on the preset character recognition model to obtain the third clinical experimental data, and the three clinical experimental data are organized and arranged according to at least one of the chronological order or the weight of at least one of the three clinical experimental data to generate the ultimate clinical experimental data. Thus, the problems of difficulty in connectivity and high error rate caused by inability to effectively integrate various acquisition methods for clinical experimental data are solved, multimodal data extraction and automatic information quality proofreading in clinical experiments are implemented based on integrating various acquisition methods for clinical experimental data and artificial intelligence.

An acquisition system for clinical experimental data according to the embodiments of the disclosure is described by referring to the drawings below.

Figure 9:
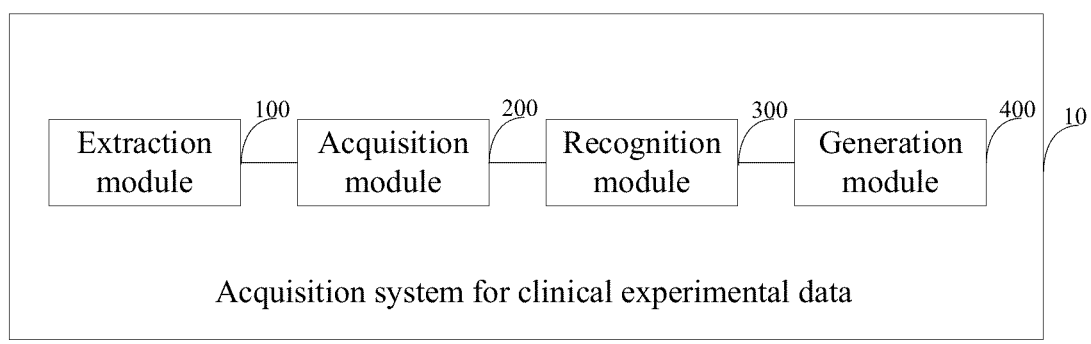
FIG. 9 illustrates a schematic diagram of an acquisition system for clinical experimental data according to an embodiment of the disclosure.

FIG. 9 illustrates a block diagram of an acquisition system for clinical experimental data according to the embodiments of the disclosure.

As shown in FIG. 9, the acquisition system for clinical experimental data 10 includes: an extraction module 100, an acquisition module 200, a recognition module 300 and a generation module 400.

The extraction module 100 is configured to extract first clinical experimental data from a target information system based on a preset extraction model for clinical experimental data.

The acquisition module 200 is configured to acquire at least on of speech input data or manual input data of a target user, and label the at least one of speech input data or manual input data to obtain second clinical experimental data.

The recognition module 300 is configured to recognize to-be-extracted clinical experimental data based on a preset character recognition model to obtain third clinical experimental data.

The generation module 400 is configured to organize and arrange the first clinical experimental data, the second clinical experimental data and the third clinical experimental data according to at least one of a chronological order or a weight of at least one of the first clinical experimental data, the second clinical experimental data and the third clinical experimental data to generate ultimate clinical experimental data.

It should be noted that, in some embodiments, the extraction module, the acquisition module, the recognition module, and the generation module described above may be implemented/embodied by one or more memories stored software modules therein and one or more processors coupled to the one or more memories and configured to execute the software modules.

In an embodiment, the generation module 400 is configured to acquire a first labor cost of the first clinical experimental data, a second labor cost of the second clinical experimental data and a third labor cost of the third clinical experimental data; determine whether each of the first labor cost, the second labor cost and the third labor cost is less than or equal to a preset labor cost threshold; and in a situation that each of the first labor cost, the second labor cost and the third labor cost is less than or equal to the preset labor cost threshold, the generation module 400 is configured to organize and arrange the first clinical experimental data, the second clinical experimental data and the third clinical experimental data according to the chronological order of at least one of the first clinical experimental data, the second clinical experimental data and the third clinical experimental data to generate the ultimate clinical experimental data; in a situation that each of the first labor cost, the second labor cost and the third labor cost is less than or equal to the preset labor cost threshold, the generation module is configure to organize and arrange the first clinical experimental data, the second clinical experimental data and the third clinical experimental data according to at least one of a chronological order or a weight of clinical experimental data corresponding to each of the one or two of the first labor cost, the second labor cost and the third labor cost to generate the ultimate clinical experimental data.

In an embodiment, the generation module 400 is configured to acquire a first weight corresponding to the first clinical experimental data, a second weight corresponding to the second clinical experimental data, and a third weight corresponding to the third clinical experimental data, organize and arrange, based on the first weight, the second weight, the third weight, the first clinical experimental data, the second clinical experimental data and the third clinical experimental data in preset order, to generate the ultimate clinical experimental data.

In an embodiment, before the extracting first clinical experiment data from a target information system based on a preset extraction model for clinical experiment data, the extraction module 100 is further configured to recognize enrollment staffs from the target information system based on at least one of a preset keyword category or a keyword number, in a situation that during a recognition process, at least one of the keyword category meeting a first threshold or the keyword number meeting a second threshold, determine the enrollment staffs meet an enrollment requirement, and enroll the enrollment staffs in a clinical experiment group after performing information privacy processing of the enrollment staffs, compare clinical experimental data of the enrollment staffs enrolled in the clinical experiment group and a classification standard to acquire comparison passed clinical experimental data, and construct the preset extraction model for clinical experimental data by using the comparison passed clinical experimental data.

In an embodiment, before the recognizing to-be-extracted clinical experiment data based on a preset character recognition model to obtain third clinical experiment data, the recognition module 300 is further configured to acquire at least one of a to-be-recognized text or a to-be-recognized image; recognize characters and a modify signing based on a preset floating distance threshold to recognize at least one of the to-be-recognized text or the to-be-recognized image to thus obtain recognized characters, concatenate the recognized characters based on a preset principle to obtain a recognized text; correct the recognized text based on a preset comparative document to obtain a corrected recognized text, and train a model based on the corrected recognized text to obtain the preset character recognition model.

In an embodiment, after the training a model based on the corrected recognized text to obtain the preset character recognition model, the recognition module 300 is further configured to update the preset comparative document based on the corrected recognized text.

In an embodiment, the preset comparative document includes at least one of a preset character pattern, a dictionary, a book, or a medical transcription.

According to the acquisition system for clinical experimental data of embodiments in the disclosure, the first clinical experimental data is extracted from the target information system based on the preset extraction model for clinical experimental data, the at least one of speech input data or manual input data of the target user are acquired, and the at least one of speech input data or manual input data are labeled to obtain the second clinical experimental data, meanwhile, the to-be-extracted clinical experimental data is recognized based on the preset character recognition model to obtain the third clinical experimental data, and the three clinical experimental data are organized and arranged according to at least one of the chronological order or the weight of at least one of the three clinical experimental data to generate the ultimate clinical experimental data. Thus, the problems of difficulty in connectivity and high error rate caused by inability to effectively integrate various acquisition methods for clinical experimental data are solved, multimodal data extraction and automatic information quality proofreading in clinical experiments are implemented based on integrating various acquisition methods for clinical experimental data and artificial intelligence.

Figure 10:
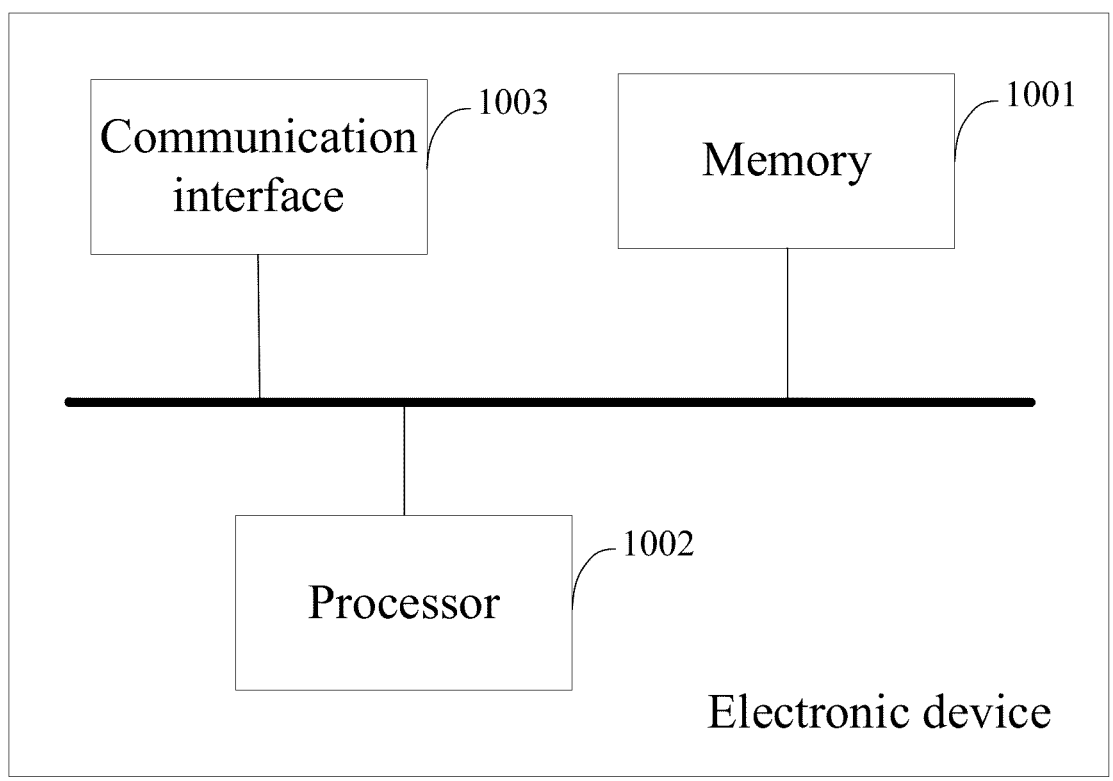
FIG. 10 illustrates a schematic structural diagram of an electronic device according to an embodiment of the disclosure.

FIG. 10 illustrates a schematic structural diagram of an electronic device provided in the embodiment of the disclosure. And the electronic device includes: a memory 1001, a processor 1002, and a computer program stored in the memory 1001 and executed in the processor 1002.

The computer program is configured to be executed by the processor 1002 to implement the acquisition method for clinical experimental data provided in the above embodiments.

In an embodiment, the electronic device further includes: a communication interface 1003. The communication interface 1003 is configured to achieve communication between the memory 1001 and the processor 1002.

The memory 1001 is configured to store the computer program executed in the processor 1002.

The memory 1001 may include a random-access memory (RAM) with high speed, and a non-volatile memory, for example, at least one disk memory.

When the memory 1001, the processor 1002, and the communication interface 1003 are independently implemented, and the communication interface 1003, the memory 1001 and the processor 1002 can be connected with each other by a bus and implement a communication with each other by the bus. The bus can be an industry standard architecture (ISA) bus, a peripheral component (PCI) bus, an extended industry standard architecture (EISA) bus and the like. The bus can be divided into an address bus, a data bus, a control bus and the like. For ease of representation, merely one thick line is used in FIG. 10, but it does not mean that there is merely one bus or one type of bus.

In an embodiment, in specific implementation, when the memory 1001, the processor 1002, and the communication interface 1003 are integrated on one chip for implementation, and the memory 1001, the processor 1002, and the communication interface 1003 can implement the communication with each other by an internal interface.

The processor 1002 may be a central processing unit (CPU), or an application specific integrated circuit (ASIC), the processor 1002 is also configured as one or more integrated circuit to implement the embodiments of the disclosure.

The embodiments of the disclosure provide a non-transitory computer-readable storage medium having a computer program stored therein, the computer program is configured to be executed by a processor to implement the above acquisition method for clinical experimental data.

In description of the specification, description of reference terms such as "an embodiment", "some embodiments", "example", "specific example" and "some examples" refers to combine specific features, structures, materials or characteristics described in the embodiment or example and included in at least one embodiment or example of the disclosure. In the specification, illustrative expression for the above terms do not necessarily refer to the same embodiment or example. Moreover, the described specific features, structures, materials or characteristics can be combined by a suitable method in any one or N embodiments or examples. Moreover, different embodiments or examples and features of the different embodiments or examples described in the specification can be combined and integrated by those skilled in the art without contradicting each other.

Moreover, terms "first", "second" are merely used for describing purpose, and cannot be understood to indicate or hint relative importance, or implicitly indicate the indicated number of technical features. Thus, features defined with "first", "second" can explicitly or implicitly include at least one of the features. In the description of the disclosure, unless otherwise specified, "N numbers" mean as least two, such as two, three.

Any process or method description in a flowchart or otherwise described herein can be understood as representing one or N module, fragment, and part of code of executable instructions of steps for implementing custom logic functions or processes, and a scope of a preferred implementation of the disclosure includes other implementations, which may not be in an order shown or discussed, and the order includes performing functions in a substantially simultaneous manner or in reverse order based on functions involved, which should be understood by those skilled in the art in the embodiments of the disclosure.

The logic and steps represented in the flowchart or otherwise described here, for example, the logic and steps can be considered as an ordered list of the executable instructions for implementing logic functions, which can be implemented in any computer-readable storage media for an instruction execution system, device or apparatus (such as a computer-based system, processor-included system or other systems can fetch instructions from the instruction execution systems, devices, or apparatuses and execute the instructions) use, or combining the instruction execution system, device or apparatus to use. For the purpose of the specification, the computer-readable storage medium can be any devices which can include, store, communicate, propagate and transfer a program for the instruction execution system, device or apparatus or combining the instruction execution system, device or apparatus to use. A more specific example of the computer-readable storage medium includes the following: an electrical connection department (i.e., an electronic device) with one or N wiring, a portable computer tray (i.e., a magnetic device), a random-access memory (RAM), a read only memory (ROM), an erasable and editable read-only memory (i.e., an erasable and programmable read-only memory abbreviated as EPROM or a flash memory), a fiber optic device, and a compact disc read-only memory (CDROM). Moreover, the computer-readable storage medium can even be papers or other suitable media on which the programs can be printed, because the programs can be obtained electronically, for example, by optically scanning paper or other media, followed by editing, interpreting, or other appropriate processing if necessary, and then stored in computer memory.

It should be understood that, each part of the disclosure can be implemented by using hardware, software, firmware or combination of the hardware, the software and the firmware. In the above embodiments, N steps or methods can be implemented by using the software or firmware stored in the memory and executed by a suitable instruction execution system. For example, if implemented in a hardware, as in another embodiment, it can be achieved by any one of the following well-known techniques or a combination of them in the art: a discrete logic circuit with logic gate for implementing logic functions on data signals, a specialized integrated circuit with suitable combination logic gates, a programmable gate array (PGA), a field programmable gate array (FPGA), and the like.

Those skilled in the art can understand that all or part of the steps carried by the above implementation method can be implemented by instructing a relevant hardware through a program, the program can be stored in a computer-readable storage medium, when the program is executed, one of the steps or a combination of the method embodiments are executed.

Moreover, in various embodiments of the disclosure, each functional unit can be integrated in a processing module, or each unit can physically exist separately, or two or more units can be integrated into one module. The above integrated modules can be implemented in both hardware and software functional module. If the integrated module is implemented in the form of the software functional module and sold or used as an independent product, it can also be stored on a computer-readable storage medium.

The storage media mentioned above can be a read-only memory, a magnetic disk, or an optical disc, etc. Although embodiments of the disclosure have been shown and described above, it can be understood that the above embodiments are exemplary and cannot be understood as a limitation to the disclosure. Those skilled in the art can make changes, modifications, substitutions, and variations to the above embodiments within the scope of the disclosure.

What is claimed is:

1. An acquisition method for clinical experimental data, comprising:

extracting first clinical experimental data from a target information system based on a preset extraction model for clinical experimental data;

acquiring at least one of speech input data or manual input data of a target user, and labeling the at least one of speech input data or manual input data to obtain second clinical experimental data;

recognizing to-be-extracted clinical experimental data based on a preset character recognition model, to obtain third clinical experimental data; and organizing and arranging the first clinical experimental data, the second clinical experimental data and the third clinical experimental data according to at least one of a chronological order or a weight of at least one of the first clinical experimental data, the second clinical experimental data and the third clinical experimental data to generate ultimate clinical experimental data;

wherein before the recognizing to-be-extracted clinical experimental data based on a preset character recognition model to obtain third clinical experimental data, the acquisition method for clinical experimental data further comprises: acquiring at least one of a to-be-recognized text or a to-be-recognized image; recognizing characters and a modifying sign based on a preset floating distance threshold to recognize the at least one of the to-be-recognized text or the to-be-recognized image to thus obtain recognized characters, concatenating the recognized characters based on a preset principle to obtain a recognized text; correcting the recognized text based on a preset comparative document to obtain a corrected recognized text, and training a model based on the corrected recognized text to obtain the preset character recognition model;

wherein the preset principle is a nearby principle or a modifying-sign-based principle, and the preset floating distance threshold is a vertical floating distance of a character from a centerline in a vertical direction; and wherein in a situation that a correction is made due to an omission in writing, the modifying sign is detected; in a situation that vertical distances of characters within the modifying sign relative to the centerline in the vertical direction fluctuate, the characters within the modifying sign are compared with the preset comparative document and a semantic check is performed; and in a situation that a sentence is unclear due to lack of the characters within the modifying sign, the characters within the modifying sign are included into the sentence.

2. The acquisition method for clinical experimental data as claimed in claim 1, wherein before the extracting first clinical experimental data from a target information system based on a preset extraction model for clinical experimental data, the acquisition method for clinical experimental data further comprises:

simulating the first clinical experimental data, the second clinical experimental data, and the third clinical experimental data, to obtain a first labor cost of the first clinical experimental data, a second labor cost of the second clinical experimental data, and a third labor cost of the third clinical experimental data, respectively;

determining whether each of the first labor cost, the second labor cost and the third labor cost is less than or equal to a preset labor cost threshold; and in a situation that each of the first labor cost, the second labor cost and the third labor cost is less than or equal to the preset labor cost threshold, organizing and arranging the first clinical experimental data, the second clinical experimental data and the third clinical experimental data according to the chronological orders of the first clinical experimental data, the second clinical experimental data and the third clinical experimental data to generate the ultimate clinical experimental data; in a situation that each of one or two of the first labor cost, the second labor cost and the third labor cost is less than or equal to the preset labor cost threshold, organizing and arranging the first clinical experimental data, the second clinical experimental data and the third clinical experimental data based on at least one of a chronological order or a weight of clinical experimental data corresponding to each of the one or two of the first labor cost, the second labor cost and the third labor cost to generate the ultimate clinical experimental data.

3. The acquisition method for clinical experimental data as claimed in claim 1, wherein the organizing and arranging the first clinical experimental data, the second clinical experimental data and the third clinical experimental data according to at least one of a chronological order or a weight of at least one of the first clinical experimental data, the second clinical experimental data and the third clinical experimental data to generate ultimate clinical experimental data, comprises:

acquiring a first weight corresponding to the first clinical experimental data, a second weight corresponding to the second clinical experimental data, and a third weight corresponding to the third clinical experimental data; and organizing and arranging, based on the first weight, the second weight, and the third weight, the first clinical experimental data, the second clinical experimental data and the third clinical experimental data in a preset order, to generate the ultimate clinical experimental data.

4. The acquisition method for clinical experimental data as claimed in claim 1, wherein before the extracting first clinical experimental data from a target information system based on a preset extraction model for clinical experimental data, the acquisition method for clinical experimental data further comprises:

recognizing enrollment staffs from the target information system based on at least one of a preset keyword category or a keyword number, in a situation that during a recognition process, at least one of the keyword category meeting a first threshold or the keyword number meeting a second threshold is satisfied, determining that the enrollment staffs meet an enrollment requirement, and enrolling the enrollment staffs in a clinical experiment group after performing information privacy processing of the enrollment staffs;

comparing clinical experimental data of the enrollment staffs enrolled in the clinical experiment group and a classification standard, to acquire comparison passed clinical experimental data; and constructing the preset extraction model for clinical experimental data by using the comparison passed clinical experimental data.

5. The acquisition method for clinical experimental data as claimed in claim 1, wherein after the training a model based on the corrected recognized text to obtain the preset character recognition model, the acquisition method for clinical experimental data further comprises:

updating the preset comparative document based on the corrected recognized text.

6. The acquisition method for clinical experimental data as claimed in claim 1, wherein the preset comparative document comprises at least one of a preset character pattern, a dictionary, a book, or a medical transcription.

7. An electronic device, comprising: a memory, a processor and a computer program stored in the memory and executed in the processor, the computer program is configured to be executed by the processor to implement the acquisition method for clinical experimental data as claimed in claim 1.

8. A non-transitory computer-readable storage medium having a computer program stored therein, wherein the computer program is configured to be executed by a processor to implement the acquisition method for clinical experimental data as claimed in claim 1.

9. An acquisition system for clinical experimental data, comprising:

an extraction module, configured to extract first clinical experimental data from a target information system based on a preset extraction model for clinical experimental data;

an acquisition module, configured to acquire at least one of speech input data or manual input data of a target user, and label the at least one of speech input data or manual input data to obtain second clinical experimental data;

a recognition module, configured to recognize to-be-extracted clinical experimental data based on a preset character recognition model, to obtain third clinical experimental data; and a generation module, configured to organize and arrange the first clinical experimental data, the second clinical experimental data and the third clinical experimental data according to at least one of a chronological order or a weight of at least one of the first clinical experimental data, the second clinical experimental data and the third clinical experimental data to generate ultimate clinical experimental data;

wherein, before the recognizing to-be-extracted clinical experimental data based on a preset character recognition model to obtain third clinical experimental data, the recognition module is further configured to acquire at least one of a to-be-recognized text or a to-be-recognized image; recognize characters and a modifying sign based on a preset floating distance threshold to recognize the at least one of the to-be-recognized text or the to-be-recognized image to thus obtain recognized characters, concatenate the recognized characters based on a preset principle to obtain a recognized text; correct the recognized text based on a preset comparative document to obtain a corrected recognized text, and train a model based on the corrected recognized text to obtain the preset character recognition model;

wherein, the preset principle is a nearby principle or a modifying-sign-based principle; and the preset floating distance threshold is a vertical floating distance of a character from a centerline in a vertical direction; and wherein, in a situation that a correction is made due to an omission in writing, the modifying sign is detected, in a situation that vertical distances of characters within the modifying sign relative to the centerline in the vertical direction fluctuate, the characters within the modifying sign are compared with the preset comparative document and a semantic check is performed, and in a situation that a sentence is unclear due to a lack of the characters within the modifying sign, the characters within the modifying sign are included into the sentence.

* * * * *